United States Patent [19]

Ogata et al.

[11] 4,370,258

[45] Jan. 25, 1983

[54] CATALYST SYSTEM FOR HYDROFORMYLATION OF OLEFINS

[75] Inventors: Ikuei Ogata; Yasuziro Kawabata, both of Tokyo; Masato Tanaka, Musashi Murayama; Teruyuki Hayashi, Tokyo, all of Japan

[73] Assignee: Agency of Industrial Science & Technology, Tokyo, Japan

[21] Appl. No.: 261,488

[22] Filed: May 7, 1981

Related U.S. Application Data

[62] Division of Ser. No. 134,100, Mar. 26, 1980, abandoned, which is a division of Ser. No. 18,879, Mar. 9, 1979, Pat. No. 4,229,381.

[30] Foreign Application Priority Data

Mar. 9, 1978 [JP]  Japan ................................. 53-26824

[51] Int. Cl.³ .................. B01J 31/18; B01J 31/12; B01J 31/21
[52] U.S. Cl. .................. 252/429 R; 252/431 R; 252/431 P; 568/454; 568/909
[58] Field of Search ..................... 252/429 R

[56] References Cited

U.S. PATENT DOCUMENTS

| | | | |
|---|---|---|---|
| 3,632,827 | 1/1972 | Smith | 252/429 R |
| 3,981,925 | 9/1976 | Schwager et al. | 260/604 H |
| 3,996,293 | 12/1976 | Knifton et al. | 260/604 H |
| 4,020,011 | 4/1977 | Nishikawa et al. | 252/429 R |
| 4,256,616 | 3/1981 | Hatanaka et al. | 252/429 R |

FOREIGN PATENT DOCUMENTS 49-20112  2/1974  Japan.
54-119407  9/1979  Japan.

*Primary Examiner*—Arthur P. Demers
*Attorney, Agent, or Firm*—Armstrong, Nikaido, Marmelstein & Kubovcik

[57] ABSTRACT

An improved hydroformylation process for preparing aldehydes by reacting olefins with synthesis gas ($H_2$ and CO) under heating and pressure is disclosed. The hydroformylation is carried out in the presence of a platinum catalyst, and assistant composed of a halide of a metal of the group IVb of the Periodic Table and a reaction promotor composed of a specific bidentate ligand of the formula $R_2X-Z-Y-Z-X-R'_2$. In this reaction, the platinum catalyst exerts a high activity, and an aldehyde mixture containing a linear isomer at a very high ratio of content is obtained as a product.

5 Claims, 1 Drawing Figure

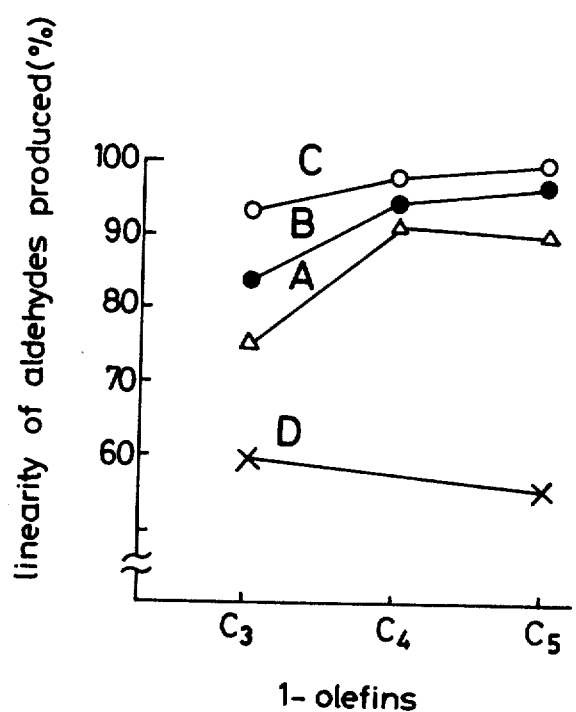

CATALYST SYSTEM FOR HYDROFORMYLATION OF OLEFINS

This is a division of prior application Ser. No. 134,100, filed Mar. 26, 1980, now abandoned, and which, in turn, is a division of prior application Ser. No. 18,879, filed Mar. 9, 1979, now U.S. Pat. No. 4,229,381.

BACKGROUND OF THE INVENTION

The present invention relates to a process for preparing aldehydes by hydroformylation of olefins.

More particularly, the invention relates to a process for catalytically hydroformylating olefins such as propylene and 1-pentene with hydrogen and carbon monoxide in the presence of a complex comprising platinum and a bidantate ligand to synthesize selectively corresponding aldehydes such as butylaldehyde and hexylaldehyde.

Hydroformylation reaction of olefins with hydrogen and carbon monoxide has been known for a long time. As catalysts for this hydroformylation reaction, there have heretofore been used cobalt-carbonyl complexes (catalysts of the first group) such as dicobalt octacarbonyl, tetracarbonyl cobalt hydride and organic phosphine-substituted cobalt carbonyl, rhodium-carbonyl complexes (catalysts of the second group) such as $Rh_4(CO)_{12}$, $RhCl(CO)(PPh_3)_2$ and $HRh(CO)(PPh_3)_3$ and platinum-phosphine complex-tin chloride catalysts (catalysts of the third group).

Catalysts of the first group are relatively low in the catalytic activity, and therefore, they cannot be used unless the temperature is elevated to a considerably high level. It is known that catalysts of the second group have a relatively high activity, but they are defective in that, in the reaction of olefins such as 1-pentene as the starting substance, the linear isomer/branched isomer ratio in the reaction product is low. Accordingly, in order to obtain a linear isomer which is industrially important, it is necessary to have a large amount of a phosphine ligand present in the reaction system. Catalysts of the third group show only an intermediate activity between those of the above-mentioned rhodium and cobalt catalysts, and when a bidantate ligand such as $Ph_2P(CH_2)_2PPh_2$ is employed, the aldehyde-forming activity is drastically lowered.

We conducted research directed to developing a catalyst having a higher activity for hydroformylation of olefins than conventional rhodium catalysts and being capable of providing a product having a higher linear isomer/branched isomer ratio. As a result, to our great surprise, it was found that when among bidantate ligands which have been considered unsuitable as promoters for platinum catalysts, a specific ligand is selected and used in combination with a platinum catalyst, the activity of the platinum catalyst is substantially enhanced over the activity of a rhodium carbonyl complex such as $RhCl(CO)(PPh_3)_2$ or $HRh(CO)(PPh_3)_3$ and an aldehyde mixture containing a linear isomer at a very high content ratio can be obtained as the reaction product. Based on this finding, we have now completed the present invention.

SUMMARY OF THE INVENTION

It is a primary object of the present invention to provide a process for the preparation of aldehydes in which the activity of a catalyst used is very high and, hence, a high conversion can be attained, and in which an aldehyde mixture having a higher linear isomer/branched isomer ratio can be obtained as the reaction product.

Other objects of the present invention will be apparent from the detailed description given hereinafter.

In accordance with the present invention, these objects can be attained by a process for the preparation of aldehydes by hydroformylation of olefins, which comprises reacting an olefin with hydrogen and carbon monoxide in the presence of a platinum catalyst and an assistant catalyst, wherein a halide of a metal selected from elements of the group IVb of the Periodic Table is used as the assistant catalyst and a bidentate ligand represented by the following general formula:

$$R_2X-Z-Y-Z-XR'_2$$

wherein R and R', which may be the same or different, stand for a group selected from the group consisting of alkyl, aryl and aralkyl groups, X is an element selected from phosphorus, arsenic and antimony, Y stands for a group selected from the group consisting of alkylene, arylene and aralkylene groups, with the proviso that the number of atoms constructing the shortest linkage chain of -Z-Y-Z- inclusive of Y is 3 to 5, and Z is a member selected from the group consisting of a methylene group and an oxygen atom, is made present in the reaction system as a reaction promoter.

This hydroformylation reaction may be carried out by the use of a solvent or without the use of a solvent.

According to the process of the present invention, a reaction product containing a linear aldehyde in a much larger amount can be prepared from a compound having a terminal vinyl group in a much shorter time than according to methods using any known hydroformylation catalysts, if reaction is carried out under the same reaction conditions. Therefore, the process of the present invention is industrially very significant and makes great contribution to industries of plastics, surfactants, synthetic fibers, perfumes, medicines and the like.

BRIEF DESCRIPTION OF THE DRAWING

The drawing shows results of experiments of hydroformylation conducted by the use of various reaction promotors and catalysts, where the relation between the kind of the 1-olefin used and the content of the linear isomer in the formed aldehydes (linearity of aldehydes produced) is illustrated.

DETAILED DESCRIPTION OF THE PREFERRED EMBODIMENTS

As the and/or ethylenically unsaturated compounds olefins that are used in the process of the present invention, there can be mentioned, for example, alkenes such as 1-alkenes, alkadienes and derivatives thereof, alkyl alkenoates such as acrylic acid esters and methacrylic acid esters, alkenyl alkylates such as vinyl esters and allyl esters of fatty acids, alkenyl alkyl ethers such as alkyl vinyl ethers, and alkenols such as allyl alcohol.

As specific examples of such and/or ethylenically unsaturated compounds olefins, there can be mentioned, ehtylene, propylene, 1-butene, 1-pentene, 1-hexene, 1-heptene, 1-dodecene, 2-ethyl-1-hexene, 1-vinyl-3-cyclohexene, styrene, methyl acrylate, methyl methacrylate, vinyl acetate, allyl ecetate, vinyl methyl ether, allyl alcohol and the like.

Among the foregoing olefins, alkenes are effectively used, and alkenes having 2 to 20 carbon atoms are especially preferred.

In the present invention, it is prefered to use a platinum catalyst in the form of a platinum-bidentate ligand complex prepared in advance, for example, Pt[Ph$_2$P(CH$_2$)$_4$PPh$_2$]Cl$_2$. However, the platinum catalyst that is used in the present invention is not limited to such complex, but any platinum compound capable of reacting with a bidentate ligand to form a platinum-carbonyl complex in the hydroformylation can be used as a catalyst precursor. As the catalyst precursor, there can be mentioned, for example, organic platinum complexes and inorganic platinum salts such as Pt(PhCN)$_2$Cl$_2$, K$_2$PtCl$_4$, Pt(PPh$_3$)$_2$Cl$_2$, Pt(COD)Cl$_2$ in which COD stands for 1,5-cyclooctadiene and PtCl$_2$.

In the process of the present invention, a halide of a metal of the group IVb of the Periodic Table is used as the assistant. Tin and germanium are preferred metals, and the halogen includes chlorine, bromine and iodine. A chloride or bromide is preferred as the halide.

As specific examples of the assistant, there can be mentioned SnCl$_2$, GeCl$_2$, PbCl$_2$, CeGeCl$_3$, SnBr$_2$ and SnI$_2$. These halides may include water of crystallization.

The reaction promoter for use in the reaction system together with the catalyst and assistant catalyst, has the following general formula

R$_2$X-Z-Y-Z-XR'$_2$.

R and R' are selected from alkyl groups having 1 to 12 carbon atoms, such as methyl, ethyl, propyl and hexyl groups, cycloalkyl groups such as cyclohexyl and methylcyclohexyl groups, aryl groups such as phenyl and tolyl groups, and aralkyl groups such as benzyl and phenetyl groups. R and R' may be the same or different. It is especially preferred that R and R' are aryl groups having 6 to 8 carbon atoms.

X stands for phosphorus, arsenic or antimony, and phosphorus is most preferred as the X.

Y is selected from alkylene, arylene and aralkylene, and these groups have preferably 1 to 10 carbon atoms. When Y is an alkylene group, a methylene chain of the formula —(CH$_2$)$_n$— in which n is a number of from 1 to 3 is preferred. Y may be an aromatic ring comprising preferaly 1 to 2 aromatic nuclei. Preferably, Y may be an alicyclic member comprising 3 to 6 membered ring.

When Y is such aromatic ring, two Z's are bonded to the aromatic ring ortho positions to each other, and when Y is such alicyclic ring, two Z's are bonded to carbon atoms of adjacent positions in the alicyclic ring.

As is apparent from the above general formula, it is one of the most important things in the invention that Y is bonded to two Z's in the form of -Z-Y-Z, and the number of atoms constructing the shortest linkage chain thereof is from 3 to 5. As specific examples of Y, there can be mentioned alkylene groups such as methylene, ethylene, propylene, cyclopropylene, cyclobutylene, cyclopentylene, cyclohexylene, norbornylene and bicyclo[2,2,2]octylene groups, arylene groups such as phenylene and naphthylene groups, and aralkylene groups such as a benzocyclobutylene group. An alicyclic or arylic group is especially preferred. These groups as Y may be substituted with an inert group such as alkyl, aryl or ester group.

When Y is an alicyclic group, the bidentate ligand includes cis-type and trans-type steric isomers. In the present invention, both isomers can be used, but the transtype isomer is preferred. Z is a methylene group or an oxygen atom.

Preferred examples of the bidentate ligand to be used in the present invention are 1,3-bis(diphenylphosphino)propane[Ph$_2$P(CH$_2$)$_3$PPh$_2$], 1,3-bis(diphenylphosphino)butane [Ph$_2$P(CH$_2$)$_4$PPh$_2$], 1,5-bis(diphenylphosphino)pentane[Ph$_2$P-(CH$_2$)$_5$PPh$_2$], 1,2-bis(diphenylphosphinomethyl)cyclopropane, 1,2-bis(diphenylphosphinomethyl)cyclobutane (hereinafter referred to as "PMCB") represented by the following formula:

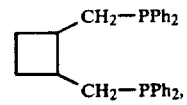

1,2-bis(diphenylphosphinoxy)cyclopentane (hereinafter referred to as "POCP") represented by the following formula:

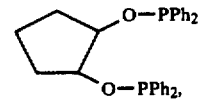

1,2-bis(diphenylphosphinomethyl)cyclophentane (hereinafter referred to as "PMCP") represented by the following formula:

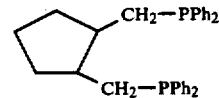

2,3-bis(diphenylphosphinomethyl)norbornane (hereinafter referred to as "PMNB") represented by the following formula:

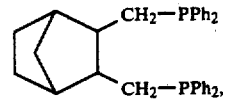

2,3-bis(diphenylphosphinomethyl)bicyclo[2,2,2]octane represented by the following formula:

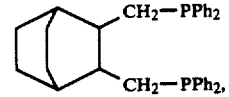

1,2-bis(diphenylphosphinomethyl)cyclohexane (hereinafter referred to as "PMCH") represented by the following formula:

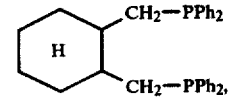

1,3-bis(diphenylphosphinoxy)cyclohexane represented by the following formula:

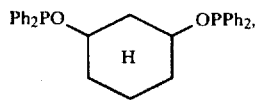

1,2-bis(diphenylphosphinomethyl)benzene (hereinafter referred to as "PMB") represented by the following formula:

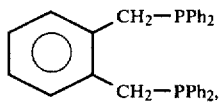

1,2-bis(diphenylphosphinoxy)benzene represented by the following formula:

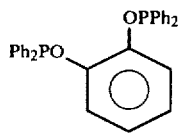

1,8-bis(diphenylphosphinomethyl)naphthalene represented by the following formula:

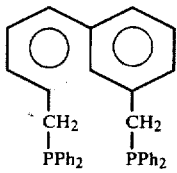

1,2-bis(diphenylarsinometyl)cyclobutane, 1,2-bis(diphenylarsinomethyl)cyclopentane (hereinafter referred to as "AMCP") represented by the following formula:

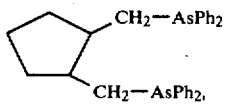

and antimony analogues thereof. However, bidentate ligands that can be used in the present invention are not limited to those exemplified above.

Reaction promotors that are especially preferably used in the present invention are PMCB, PMCP, POCP, PMNB and substituted derivatives thereof.

In practising the process of the present invention, a platinum catalyst and a bidentate ligand or a complex of both and an olefin are charged in a pressure vessel and the olefin is reacted with a compressed mixed gas of carbon monoxide and hydrogen (synthesis gas). A solvent need not be used for this reaction, but the reaction may be carried out in a solvent. As the solvent, there can be used, for example, aliphatic saturated hydrocarbons such as hexane and heptane, alicyclic hydrocarbons such as cyclohexane and Decalin, aromatic hydrocarbons such as benzene and toluene, ethers such as diethyl ether and tetrahydrofuran, halogenated hydrocarbons such as methylene chloride and chlorobanzene, ketones such as acetone and methylethyl ketone, and alcohols such as methanol and ethanol. When the process is carried out in industry and when the catalyst must be recycled and used repeatedly, it is preferred to use a high-boiling solvent capable of retaining the catalyst in the form of a solution after distillation of the product. The amount of the solvent used is not particularly critical. However, if the amount of the solvent is excessive, the reaction speed is reduced. Accordingly, it is preferred that the solvent is used in a minimum necessary amount. More specifically, it is ordinarily preferred that the volume of the solvent is less than 10 times the volume of the olefin, though the preferred amount of the solvent varies according to its kind.

In the present invention, the platinum catalyst is used in a small amount. The amount of the catalyst used is determined depending on the reaction conditions and the kind of the olefin. In general, however, the platinum catalyst is used in an amount of $1.0 \times 10^{-5}$ to $1.0 \times 10^{-3}$ mole as metallic platinum, per mole of the olefin.

The amount of the bidentate ligand to be made present in the reaction system together with the platinum catalyst is determined according to its coordination power and the reaction conditions. In general, the ligand is used in an amount of up to 10 moles, preferably 0.5 to 5 moles, per mole of platinum.

The halide of a metal of the group IVb of the Periodic Table as the assistant is used in an amount of up to 50 moles, preferably 0.5 to 20 moles, per mole of platinum.

In practising the process of the present invention, the carbon monoxide/hydrogen molar ratio in the mixed gas is adjusted to 0.1 to 10, preferably 0.5 to 3.0.

Each of carbon monoxide and hydrogen is consumed in an amount of 1 mole per mole of the olefin. The total pressure of the mixed gas of carbon monoxide and hydrogen is adjusted to 5 to 500 Barr, preferably 50 to 200 Barr. As the reaction temperature is lower, the selectivity to aldehydes is higher, but from the viewpoint of the reaction speed, the reaction is preferably carried out at 40° to 200° C., especially 50° to 150° C.

According to the process of the present invention, there can be obtained various aldehydes such as propyl aldehyde, n-butylaldehyde, n-pentyl aldehyde, n-hexyl aldehyde, n-octyl aldehyde, 3-(3-cyclohexenyl)propionaldehyde, 2-phenylpropyl aldehyde, 3-phenylpropyl aldehyde, methyl 3-formylpropionate, methyl 3-formyl-2-methylpropionate, 3-acetoxypropyl aldehyde, 3-methoxypropyl aldehyde and 3-hydroxybutylaldehyde. These aldehydes may be used as final products or industrial raw materials as they are or after they have been converted to alcohols or acids by hydrogenation or oxidation.

The present invention will now be described by reference to the following Examples that by no means limit the scope of the invention. When results of these Examples are compared with results of Comparative Examples illustrating reactions using conventional unidentate ligand catalysts and rhodium catalysts, advantages and characteristics of the present invention will be apparent.

COMPARATIVE EXAMPLES 1 TO 7

A stainless steel pressure-resistant reaction tube having an inner capacity of 50 ml was charged with 25 mg of Pt(PPh$_3$)$_2$Cl$_2$ and 36.1 mg ($1.6 \times 10^{-4}$ mole) of stannous chloride (SnCl$_2$.2H$_2$O), and the inner atmosphere was replaced by nitrogen and 6 ml of ethylbenzene was introduced as a solvent. Further, 3 ml ($3.2 \times 10^{-2}$ mole) of 1-butene was added to the charge and a 1:1 mixed gas of carbon monoxide and hydrogen was compressed up to under 100 atmospheres at 0° C. ($P_{CO}=P_{H2}=50$ atmospheres). The reaction vessel was dipped in an oil bath maintained at 100° C. and agitation was started. When this state was kept for 10 hours, reduction of the pressure on a pressure gauge was stopped. The reaction speed was determined by plotting the pressure in the reaction vessel as a function of the time. On completion of the reaction, the reaction vessel and the content were cooled, and the reaction product solution was anylyzed by gas chromatography to obtain results shown in Table 1.

the aldehyde produced is lower than that attained when $Pt(PPh_3)_2Cl_2$ is used.

EXAMPLES 1 TO 6

According to the procedure described in Comparative Example 1, hydroformylation was carried out under conditions shown in Table 2 to obtain resulsts shown in Table 2.

When the bidentate ligand $R_2X$-$Z$-$Y$-$Z$-$XR_2$ where R is Ph, X is P, Z is $CH_2$ and Y is $(CH_2)_{n-2}$, namely $Ph_2P(CH_2)_nPPh_2$, is employed, if n is 3,4 or 5, the reac-

TABLE 1

| Comparative Example Nos. | Catalysts[a] | Ligand (amount used, mole) | Reaction Time (hours) | Relative Rate[b] | Yield (%) of Aldehydes | Content (%) of Linear Isomer in Aldehydes |
|---|---|---|---|---|---|---|
| 1. | $Pt(PPh_3)_2Cl_2$ | — | 10.5 | 96 | 38.8 | 80 |
| 2. | $Pt(PhCN)_2Cl_2$ | $PPh_3$ ($6.4 \times 10^{-5}$) | 7.0 | 100 | 56.1 | 80 |
| 3. | " | $Ph_2PCh_2PPh_2$ ($3.2 \times 10^{-5}$) | 24.0[c] | 4 | 2.4 | 79 |
| 4. | " | $Ph_2PCH_2CH_2PPh_2$ ($3.2 \times 10^{-5}$) | 24.0[c] | 13 | 36.2 | 80 |
| 5. | " | $Ph_2P(CH_2)_6PPh_2$ ($3.2 \times 10^{-5}$) | 24.0 | 45 | 28.9 | 83 |
| 6. | " | $Ph_2P(CH_2)_{10}PPh_2$ ($3.2 \times 10^{-5}$) | 24.0 | 50 | 39.4 | 91 |
| 7. | $RhCl(PPh_3)_3$ | — | 5.0 | 168 | 95.0 | 66 |

Notes
[a] The amount used was $3.2 \times 10^{-5}$ mole.
[b] The relative rate was calculated based on the assumption that the gradient of the curve of the reaction time vs. the pressure reduction in Comparative Example 2 was 100.
[c] The reaction was stopped after passage of 24 hours even if the pressure reduction was not completed.

From the foregoing results of comparative experiments to confirm the effects of the conventional techniques, the following can be seen.

Results of Comparative Examples 1 and 2 illustrate that whether the $Pt(PPh_3)_2Cl_2$ complex is used as the platinum catalyst or $Pt(PhCN)_2Cl_2$ and $PPh_3$ in an amount of 2 moles per atom of platinum are mixed in the reaction vessel, the obtained results are not substantially different. From the results of Comparative Example 4, tion speed is much higher than the reaction speed attained when $PPh_3$ is used, and the reaction speed is especially high if n is 4. In the case where n is 4, if the methylene groups constitute a part of a cyclic structure as in Examples 4, 5 or 6, especially in Examples 4 and 5, the reaction speed is 18 to 19 times as high as the reaction speed attained by the ligand $PPh_3$ in Comparative Example 2, and in this case, the linear isomer/branched isomer ratio increased from 95/5 to 80/20.

TABLE 2

| Example Nos.[a] | Catalysts | Ligand | Reaction Time (hour) | Relative Rate[c] | Yield (%) of Aldehydes | Content (%) of Linear Isomer in Aldehydes |
|---|---|---|---|---|---|---|
| 1. | $Pt(PhCN)_2Cl_2$ | $Ph_2P(CH_2)_3PPh_2$ | 4.0 | 220 | 57.0 | 65 |
| 2. | " | $Ph_2P(CH_2)_4PPh_2$ | 4.0 | 275 | 83.9 | 85 |
| 3. | " | $Ph_2P(CH_2)_5PPh_2$ | 5.0 | 125 | 60.7 | 89 |
| 4. | " | $PMCB$[b] | 1.0 | 1820 | 69.2 | 95 |
| 5. | $Pt(PMCB)_2Cl_2$[b] | — | 1.0 | 1910 | 73.5 | 95 |
| 6. | $Pt(PhCN)_2Cl_2$ | $PMCP$[b] | 1.5 | 1380 | 70.0 | 90 |

Notes:
[a] The reaction was carried out under conditions described below.
1-butene: $3.2 \times 10^{-2}$ mole
catalyst: $3.2 \times 10^{-5}$ mole
$SnCl_2.2H_2O$: $1.6 \times 10^{-4}$ mole
ethylbenzene: 6 ml
reaction temperature: 100° C.
$P_{CO} = P_{H2} = 50$ atmospheres
[b] The trans-isomer was used. PMCB and PMCP are hereinbefore mentioned.
[c] See Table 1.

it is seen that when 1,2-bis(diphenylphosphino)ethane which is readily chelated and is often used as a bidentate ligand is employed, the reaction is remarkably inhibited as compared with the case where $PPh_3$ is employed. Results of Comparative Examples 5 and 6 illustrate that also bidentate ligands which are unable to chelate reduce the reduction speed. Results of Comparative Example 7 demonstrate that $RhCl(PPh_3)_3$ which is known to have a high activity for hydroformylation enhances the reaction speed but the content of the linear isomer in

EXAMPLES 7 TO 10 AND COMPARATIVE EXAMPLES 8 AND 9

In order to clarify the influence of the size of the ring on the rate and selectivity of the reaction, when Y of the bidentate ligand $R_2X$-$Z$-$Y$-$Z$-$XR'_2$ has a cyclic structure, the hydroformylation of 1-pentene as the olefin was carried out according to the present invention. Reaction conditions and results obtained are described below.

Hydrogen and carbon monoxide were introduced under pressure into an autoclave charged with the catalyst, bidentate ligand, stannous chloride and benzene. The partial pressure of each of hydrogen and carbon monoxide was 50 atmospheres. The pre-treatment was conducted at 100° C. for 3 hours, and a predetermined amount of 1-pentene was charged into the autoclave and predetermined amounts of hydrogen and carbon monoxide were recharged to effect reaction. Results obtained are shown in Table 3.

From comparing results of Examples 8, 9 and 10 shown in Table 3, it will readily be understood that as the size of the ring Y is diminished, the reaction speed is remarkably increased and also the linear isomer/branched isomer ratio in the formed aldehydes is increased.

stantially completed before the temperature in the reaction vessel reached 100° C. Therefore, the reaction was carried out while reducing the catalyst concentration to 1/10. Obtained results are shown in Table 4.

From comparison of results of Examples 12 and 13, it will readily be understood that even if Z in the ligand is changed to oxygen atom from the methylene group, the reaction rate is not substantially changed. From comparison of results of Examples 14, 15 and 16 where Y has a 6-membered ring structure, it will readily be understood that the results obtained are slightly better when two Z groups bonded to Y are located at the trans-positions, than results obtained when Z groups are bonded to Y at the cis-positions, but in each case, the results are inferior to results obtained when two Z groups are situated on the plane. It will readily be seen

TABLE 3

| Example Nos.[a] | Catalyst[b] | Ligand Kind | Amount Used (mole) | Reaction Time (hour) | Conversion (%) | Relative Rate[d] |
|---|---|---|---|---|---|---|
| 7. | Pt(PhCN)$_2$Cl$_2$ | Ph$_2$P(CH$_2$)$_4$PPh$_2$ | $3.2 \times 10^{-5}$ | 1.5 | 100 | 400 |
| 8. | " | PMCH[c] | $3.2 \times 10^{-5}$ | 2.0 | 100 | 340 |
| 9. | " | PMCP[c] | $3.2 \times 10^{-5}$ | 1 | 100 | 720 |
| 10. | " | PMCB[c] | $3.2 \times 10^{-5}$ | 0.5 | 100 | 1090 |
| Comparative Example No. 8 | Pt(PhCN)$_2$Cl$_2$ | PPh$_3$ | $6.4 \times 10^{-5}$ | 5 | 87 | 100 |
| Comparative Example No. 9 | PhCl(CO)(PPh$_3$)$_2$ | — | — | 5 | 100 | 110 |

| Example Nos.[a] | Yields (%) Hydrogenation Product (n-pentane) | Isomerization Product (2-pentene) | Aldehydes | Content (%) of Linear Isomer in Aldehydes | Polymer Content (%) |
|---|---|---|---|---|---|
| 7. | 12.6 | 13.9 | 74.8 | 92 | 0 |
| 8. | 10.0 | 12.7 | 68.6 | 92 | 6.8 |
| 9. | 7.4 | 10.1 | 75.0 | 96 | 7.8 |
| 10. | 6.7 | 16.5 | 76.9 | 99 | 0 |
| Comparative Example No. 8 | 3.6 | 8.6 | 65.8 | 91 | 22.0 |
| Comparative Example No. 9 | 0 | 2.2 | 97.8 | 62 | 0 |

Notes
[a]The reaction was carried out under the following conditions:
1-pentene: 3 ml
SnCl$_2$.2H$_2$O: [Pt]/[Sn] = 1/5
benzene (solvent): 18 ml
reaction temperature: 100° C.
[b]The catalyst was used in an amount of $3.2 \times 10^{-5}$ mole.
[c]The trans-isomer was used. PMCH, PMCP and PMCB are hereinbefore mentioned.
[d]The relative rate was calculated based on the assumption that the gradient of the curve of the reaction time and the pressure reduction in Comparative Example 8 was 100.

EXAMPLES 11 TO 19 AND COMPARATIVE EXAMPLES 10 AND 11

The reaction was carried out in the same manner as in Examples 8, 9 and 10 while changing the catalyst concentration. In Examples 8, 9 and 10 shownin in Table 3, the reaction rate was so high that the reaction was subthat in each of these Examples 14, 15 and 16, the reaction rate is higher than that by use of PPh$_3$. Further, from comparison of results of Examples 14 and 18, it will be apparent that even if Y has a 6-membered ring structure, a remarkably high reaction rate is obtainable if the rigidity of the 6-membered ring is increased by intracircular crosslinkage.

TABLE 4

| Example Nos. | Catalyst | Ligand Kind | Amount Used (mole) | Reaction Temperature (°C.) | Reaction Time (hour) | Conversion (%) | Relative Rate[d] |
|---|---|---|---|---|---|---|---|
| 11. | Pt(PhCN)$_2$Cl$_2$[f] | PMCB[a] | $3.2 \times 10^{-6}$ | 100 | 3[c] | 100 | 3100 |
| 12. | " | POCP[a] | " | 100 | 5.5 | 100 | 1800 |
| 13. | " | PMCP[a] | " | 100 | 5 | 100 | 1500 |
| 14. | " | PMCH[a] | " | 100 | 18 | 100 | 600 |
| 15. | " | PMCH[b] | " | 100 | 19 | 100 | 400 |
| 16. | " | PMB | " | 100 | 10 | 44.5 | 800 |
| 17. | " | PMCB[e] | " | 100 | 9 | 100 | 1070 |
| 18. | " | PMNB[a] | " | 100 | 2.5 | 100 | 2780 |
| 19. | Pt(PhCN)$_2$Cl$_2$[g] | PMCB[a] | $3.2 \times 10^{-5}$ | 70 | 2[c] | 100 | 4000 |
| Comparative Example No. 10 | Pt(PhCN)$_2$Cl$_2$[f] | PPh$_3$ | $6.4 \times 10^{-6}$ | 100 | 24 | 3.8 | 100 |
| Comparative | | | | | | | |

TABLE 4-continued

| Example No. 11 | HRh(CO)(PPh$_3$)$_3$[g] | — | — | 70 | 5 | 100 | 1200 |

| Example Nos. | Yields (%) Hydrogenation Product (n-pentane) | Yields (%) Isomerization Product (2-pentene) | Yields (%) Aldehydes | Content (%) of Linear Isomer in Aldehydes | Polymer Content (%) |
| --- | --- | --- | --- | --- | --- |
| 11. | 6.4 | 13.4 | 79.0 | 98 | 0.2 |
| 12. | 11.4 | 26.1 | 62.0 | 93 | 0.5 |
| 13. | 7.8 | 12.3 | 75.7 | 96 | 1.8 |
| 14. | 13.4 | 10.5 | 76.6 | 89 | 0 |
| 15. | 8.1 | 19.9 | 72.0 | 90 | 0 |
| 16. | 9.5 | 20.7 | 65.3 | 91 | 0 |
| 17. | 8.2 | 19.5 | 72.3 | 98 | 0 |
| 18. | 8.5 | 18.6 | 72.9 | 99 | 0 |
| 19. | 3.5 | 7.6 | 88.6 | 99 | 0.3 |
| Comparative Example No. 10 | 0.3 | 0.5 | 3.0 | 92 | 0.0 |
| Comparative Example No. 11 | 0.0 | 1.1 | 98.9 | 70 | 0 |

Notes:
[a]The trans-isomer was used.
[b]The cis-isomer was used.
[c]When the catalyst concentration is low, there is sometimes present an induction period prior to initiation of reaction. Accordingly, there is no close correlation between the reaction time and the reaction speed.
[d]The relative rate was calculated based on the assumption that the reaction speed in Comparative Example 10 was 100. The reaction speed is substantially proportional in the first order to the catalyst concentration.
[e]Solvent was not used.
[f]The catalyst was used in an amount of 3.2 × 10$^{-6}$ mole.
[g]The catalyst was used in an amount of 3.2 × 10$^{-5}$ mole.
The abbreviations such as PMCB etc. are hereinbefore mentioned.

In Examples shown in Table 3, unknown substances considered to be polymers of formed aldehydes were detected. In Examples 11 to 18 where the catalyst concentration was reduced, such substances were hardly formed. Example 19 and Comparative Example 11 were carried out at a relatively low temperature. From the results of these Examples, it is seen that, when the catalyst system of the present invention is used, occurrence of hydrogenation or isomerization is slightly more conspicuous than in the case of the conventional rhodium catalyst system but the linear isomer/branched isomer ratio is much higher than in the case of the conventional rhodium catalyst system. More specifically, the yield of the linear aldehyde obtained in Comparative Example 11 is 69.7% based on the starting olefin (=98.9×0.7). On the other hand, in Example 19, the yield of the linear aldehyde is 87.7% (=88.6×0.99). Further, the reaction speed is Example 19 is 3.2 times as high as the reaction speed in Comparative Example 11. Accordingly, it is apparent that the present invention is excellent over the conventional technique using a rhodium catalyst.

EXAMPLE 20

According to the procedure described in Examples 11 to 18, hydroformylation of propylene, 1-butene and 1-pentene was carried out at 100° C. by use of a bidentate ligand having a ring structure and the selectivity to the linear aldehyde was examined. For comparison, an experiment was similarly conducted by the use of HRh(CO)(PPh$_3$)$_3$ as the catalyst. Results obtained are shown in the accompanying drawing, where line A shows results obtained when the following compound was used as the trans-substituted cyclic bidentate ligand in addition to the platinum catalyst:

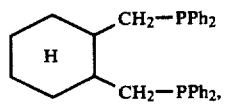

curve B shows results obtained by the following cyclic ligand:

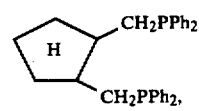

curve C shows the results obtained by the following cyclic ligand:

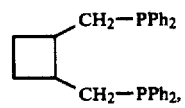

and line D shows the results obtained by using HRh(CO)(PPh$_3$)$_3$ as the catalyst.

From these results, the following can be seen.

The platinum catalyst system of the present invention provides a little larger amount of the isomerization product than the unknown rhodium complex catalyst. However, in case of propylene, which is industrially most important as the starting material of hydroformylation, isomerization does not cause any trouble or problem. Accordingly, the catalyst system of the present invention is superior to the conventional rhodium complex catalyst in that the reaction speed is high and selective formation of linear aldehyde is extremely high.

EXAMPLES 21 TO 26

Hydroformylation was carried out according to procedures of Examples 7 to 10 while changing broadly the kinds of the catalyst, assistant catalyst and bidentate ligand. Some of these experiments are reported as Examples 21 to 26 which are reported in Table 5.

From the results shown in Table 5, it will readily be understood that all the ligands included in the scope of the present invention can give a reaction speed higher than that attained by PPh$_3$, though the degree of elevation of the reaction rate is varied to some extent according to the kind of the ligand.

TABLE 5

| Example Nos. | Catalyst[a] | Assistant[b] | Ligand[c] | Reaction Time (hour) | Conversion (%) | Relative Rate[d] |
|---|---|---|---|---|---|---|
| 21. | $Pt(PhCN)_2Cl_2$ | $SnCl_2.2H_2O$ | AMCP | 1.0 | 100 | 545 |
| 22. | " | $SnCl_2$ | PMCP | 0.5 | 100 | 890 |
| 23. | " | $CsGeCl_3$ | PMCP | 3.0 | 100 | 224 |
| 24.[e] | " | $SnCl_2.2H_2O$ | PMCP | 1.0 | 100 | 914 |
| 25. | " | $SnBr_2$ | PMCP | 1.0 | 100 | 620 |
| 26 | $Pt(COD)Cl_2$[f] | $SnCl_2.2H_2O$ | PMCP | 1.0 | 100 | 1030 |

| | Yields (%) | | | | |
|---|---|---|---|---|---|
| Example Nos. | Hydrogenation Product (n-pentane) | Isomerization Product (2-pentene) | Aldehydes | Content (%) of Linear Isomer in Aldehydes | Polymer Content (%) |
| 21. | 11.5 | 4.0 | 45.5 | 86 | 39.0 |
| 22. | 8.0 | 14.7 | 77.9 | 96 | 0 |
| 23. | 22.5 | 3.0 | 74.5 | 96 | 0 |
| 24. | 10.4 | 21.2 | 68.4 | 90 | 0 |
| 25. | 9.8 | 24.7 | 54.4 | 96 | 10.8 |
| 26. | 10.4 | 13.7 | 74.9 | 95 | 0 |

What we claim is:

1. A catalyst system for hydroformylation of olefins, which comprises, (1) at least $1 \times 10^{-5}$ mole of a platinum catalyst, calculated as metallic platinum, per mole of said olefin; (2) 0.5 to 50 moles of an assistant catalyst per mole of said platinum catalyst, calculated as metallic platinum, the assistant catalyst being selected from the group consisting of halides of metals of group IVb of the periodic table; and (3) 0.5 to 10 moles of a bidentate ligand reaction promoter per mole of said platinum catalyst, calculated as metallic platinum, said bidentate ligand having the general formula:

$R_2X-Z-Y-Z-XR'_2$ wherein:
(a) R and R', which may be the same or different, are selected from the group consisting of (i) an alkyl group having 1–12 carbon atoms, (ii) a cycloalkyl group having 6–7 carbon atoms, (iii) an aryl group having 6–10 carbon atoms, and (iv) an aralkyl group having 7–8 carbon atoms;
(b) X is phosphorus, arsenic or antimony;
(c) Y is an alkylene group having 1–3 carbon atoms, a phenylene group, a naphthylene group, or an alicyclic group having a 3- to 6-membered ring; and
(d) Z is a methylene group or oxygen.

2. A catalyst system according to claim 1 wherein Y is an alicyclic group having a 3- to 6-membered ring and the two Z's are bonded to adjacent carbon atoms of the alicyclic group.

3. A catalyst system according to claim 1 wherein Y is a phenylene group or a naphthylene group and the two Z's are bonded to adjacent carbon atoms of said group.

4. A catalytic system according to claim 1 wherein Y is an alkylene group having 2–3 carbon atoms.

5. A catalyst system according to claim 1 wherein the number of atoms constructing the shortest linkage chain of -Z-Y-Z- inclusive of Y is 3 to 5.

* * * * *